tion delay circuit, a reception delay circuit, a peak value detection circuit, a calculus discrimination circuit, a spectrum analyzer, a destruction degree discrimination circuit, an external switch, and a CRT.

United States Patent [19]
Aida et al.

[11] Patent Number: 5,358,466
[45] Date of Patent: Oct. 25, 1994

[54] APPARATUS FOR DESTROYING A CALCULUS

[75] Inventors: Satoshi Aida, Tokyo; Katsuhiko Fujimoto, Kawasaki; Kaoru Suzuki, Utsunomiya; Nobuyuki Iwama, Tochigi; Akinori Ishida, Kawasaki, all of Japan

[73] Assignee: Kabushiki Kaisha Toshiba, Kawasaki, Japan

[21] Appl. No.: 868,414

[22] Filed: Apr. 15, 1992

[30] Foreign Application Priority Data

Apr. 15, 1991 [JP] Japan .................................. 3-11104
May 10, 1991 [JP] Japan .................................. 3-105863
Mar. 25, 1992 [JP] Japan .................................. 4-66823

[51] Int. Cl.⁵ ............................................. A61H 1/00
[52] U.S. Cl. ..................................... 601/4; 128/660.03
[58] Field of Search ........ 128/24 EL, 24 AA, 660.03; 601/2, 4

[56] References Cited

U.S. PATENT DOCUMENTS

| 3,958,559 | 5/1976 | Glenn et al. | 128/663.01 |
|---|---|---|---|
| 4,437,348 | 3/1984 | Sasaki | 128/661.01 |
| 4,526,168 | 7/1985 | Hassler et al. | 128/24 EL |
| 4,528,854 | 7/1985 | Shimazaki . | |
| 4,757,820 | 7/1988 | Itoh | 128/24 AA |
| 4,803,995 | 2/1989 | Ishida et al. | 128/660.03 |
| 4,986,259 | 1/1991 | Aida et al. | 128/660.03 |
| 5,009,232 | 4/1991 | Hassler et al. | 128/660.03 |
| 5,076,277 | 12/1991 | Iwama et al. | 128/24 EL |

FOREIGN PATENT DOCUMENTS

| 0031510 | 7/1981 | European Pat. Off. . | |
|---|---|---|---|
| 0460536 | 12/1991 | European Pat. Off. | 128/24 EL |
| 3617032 | 1/1987 | Fed. Rep. of Germany . | |
| 3913023 | 11/1989 | Fed. Rep. of Germany . | |

Primary Examiner—Lee S. Cohen
Assistant Examiner—Brian L. Casler
Attorney, Agent, or Firm—Oblon; Spivak, McClelland, Maier & Neustadt

[57] ABSTRACT

An apparatus for destroying a calculus includes an ultrasonic wave generating unit capable of setting a plurality of piezo-electric devices in a drive/reception mode by phase control, a peak value detecting unit for detecting a peak value, in a predetermined time width, of an echo signal in a reception signal received by the piezo-electric devices, a first comparing unit for comparing the peak value detected by the peak value detecting unit with a first predetermined threshold value, a frequency analyzing unit for analyzing a frequency component, in the predetermined time width, of the echo signal in the reception signal, a calculating unit for calculating a predetermined characteristic value on the basis of frequency component data obtained by the frequency analyzing unit, a second comparing unit for comparing the characteristic value obtained by the calculating unit with a second predetermined threshold value, and a display unit for displaying a comparison result of the first comparing unit with a comparison result of the second comparing unit.

2 Claims, 12 Drawing Sheets

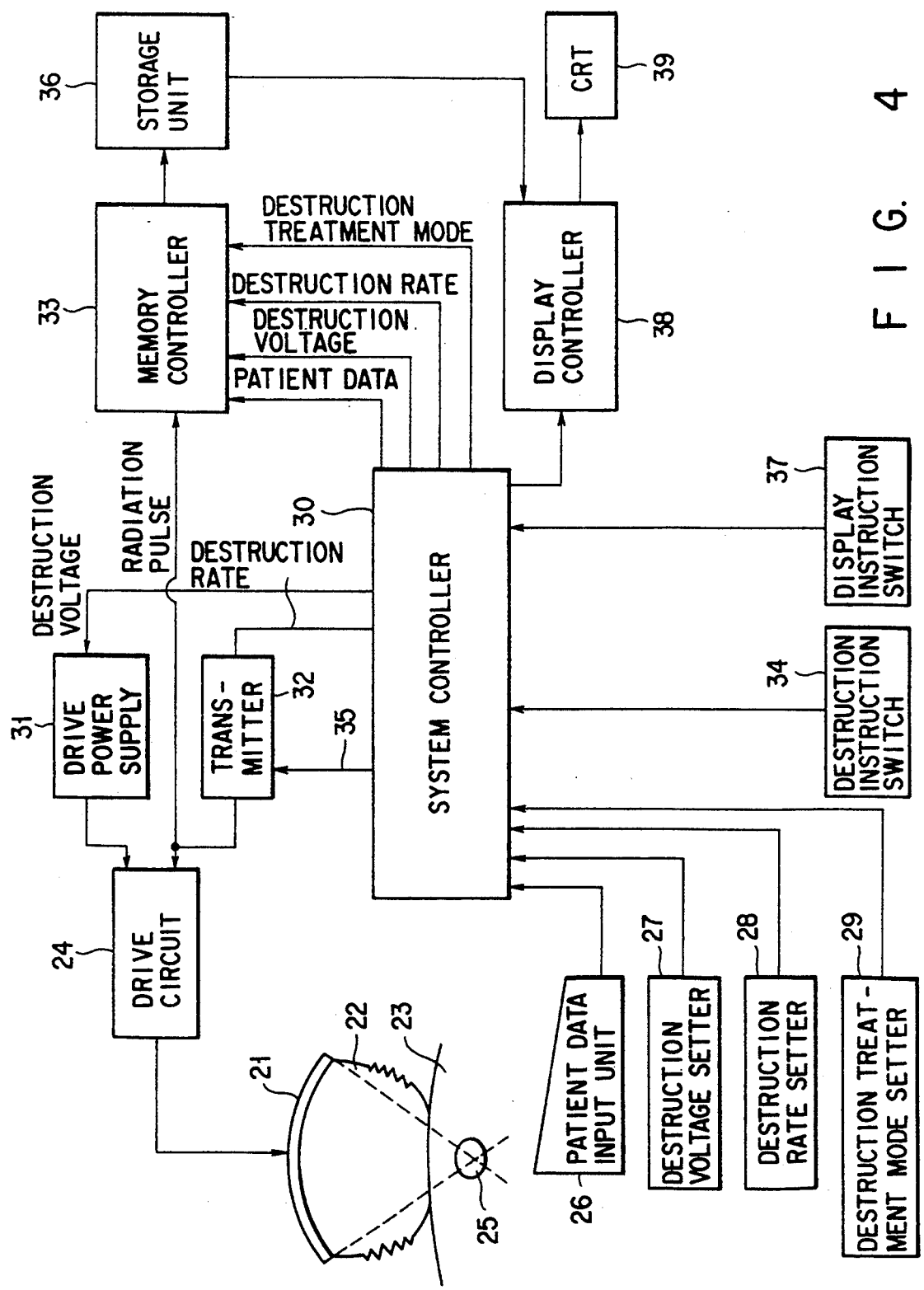
F I G. 4

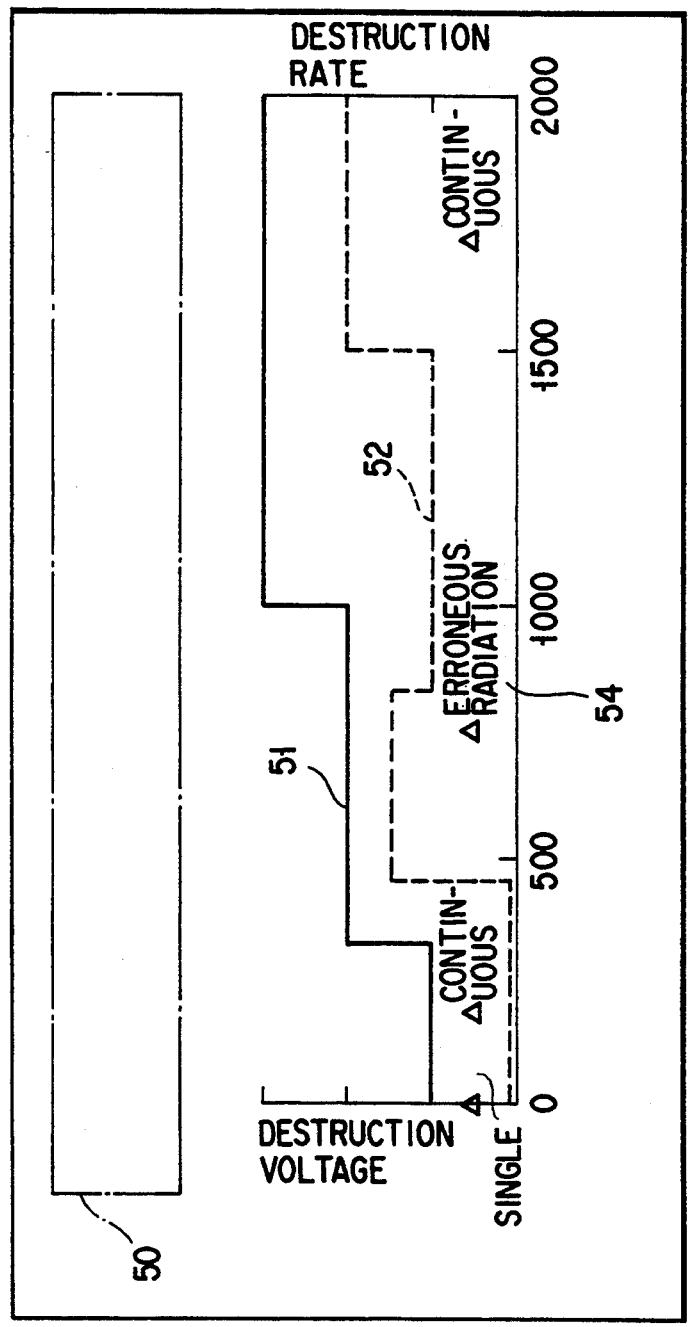
F I G. 6

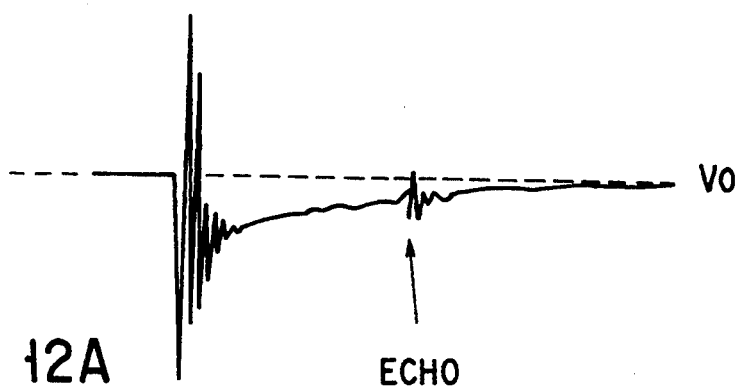
F I G. 12A
ECHO
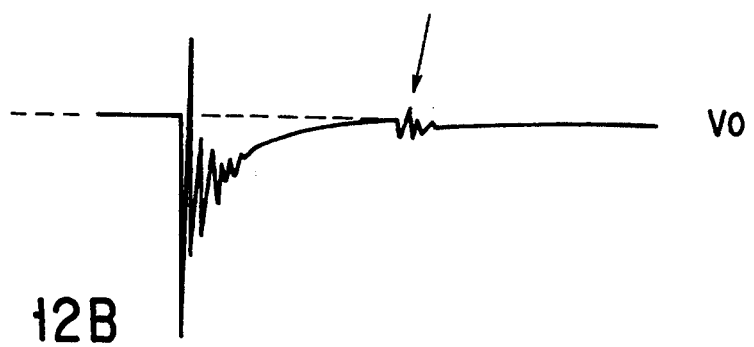
F I G. 12B
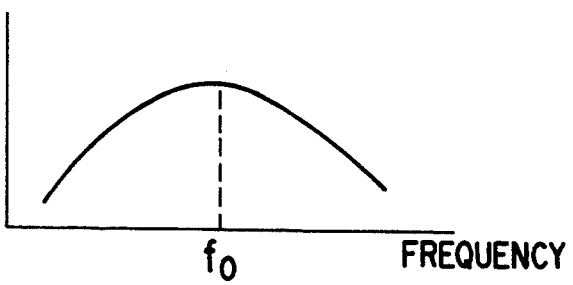
F I G. 13A
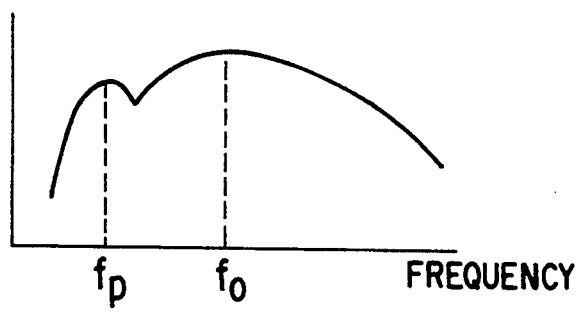
F I G. 13B

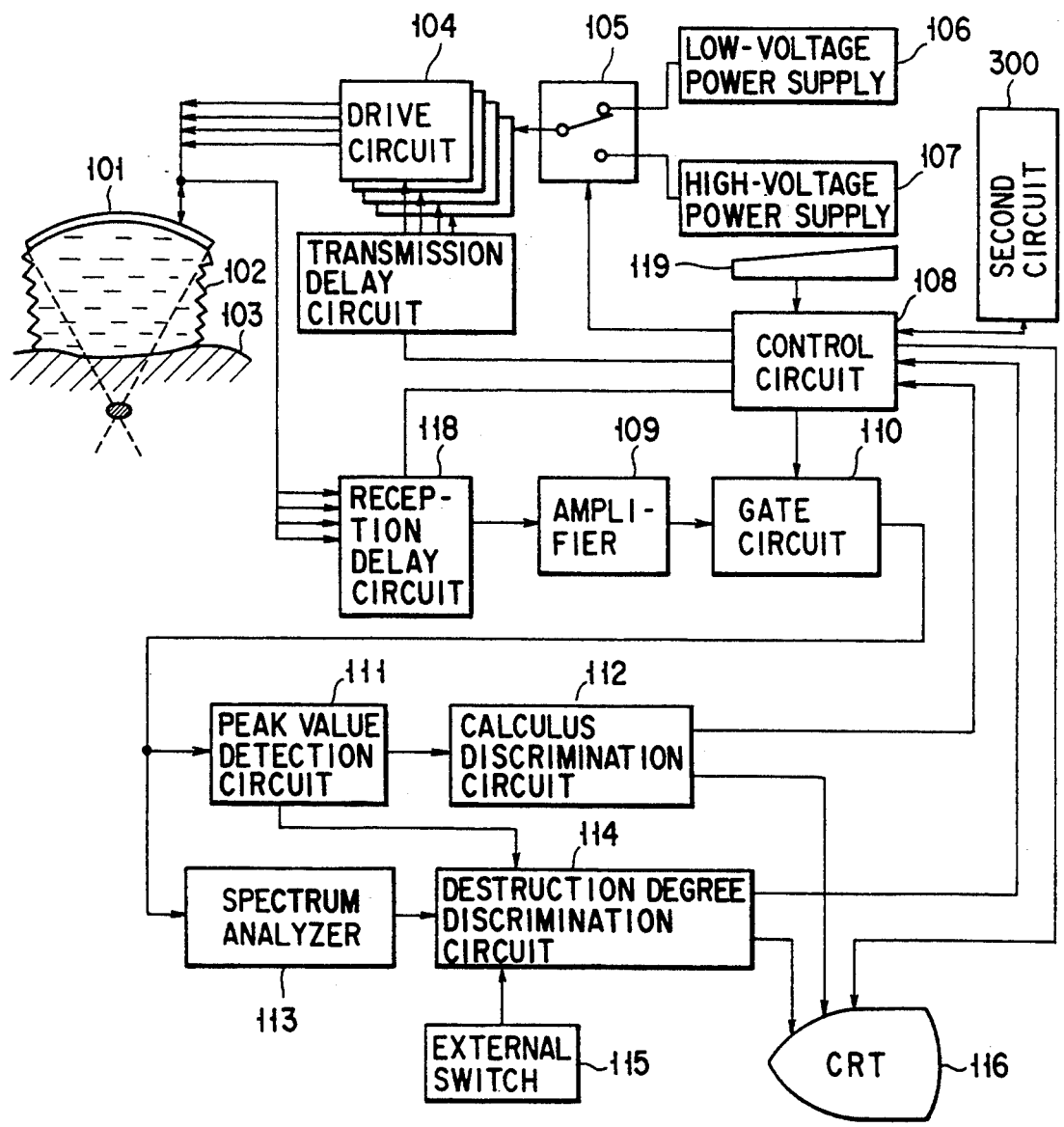
F I G. 15

APPARATUS FOR DESTROYING A CALCULUS

BACKGROUND OF THE INVENTION

1. Field of the Invention

The present invention relates to a shock wave calculus destroying apparatus and, more particularly, to an apparatus for destroying a calculus which uses an ultrasonic imaging unit to position a calculus and confirm the destruction state of the calculus.

2. Description of the Related Art

Recently, in treatment of a renal calculus or a gallstone, a method of non-invasive treatment using a shock wave is popularly used. Typical examples of a shock wave generating source include underwater discharge, electromagnetic induction, and a piezo-electric device, which have individual features. Various methods are used for positioning a calculus at a focal point of a shock wave and for confirming the destruction state of the calculus. Especially, a method of generating a shock wave by using a piezo-electric device has an excellent feature. More specifically, no consumable is used, the intensity of the shock wave can be arbitrarily controlled, and the focal point can be controlled by controlling the phase of the drive pulse applied to a plurality of piezo-electric devices (e.g., Published Unexamined Japanese Patent Application No. 60-145131 and U.S. Pat. No. 4,526,168).

In the initial stage of development of an apparatus for destroying a calculus, positioning and confirmation of the destruction state were performed by using X-ray TVs in two directions (e.g., Published Unexamined Japanese Patent Application No. 62-94144). With this method, however, the patient and the operator can be exposed to X-ray radiation, and continuous monitoring cannot be performed in order to minimize the X-ray dose as much as possible.

In contrast to this, in order to perform positioning and destruction state confirmation, recently, a method using an ultrasonic imaging unit is often employed (e.g., Published Unexamined Japanese Patent Application No. 60-145131). According to this method, a location to install an ultrasonic probe is limited to the inside or outside of a shock wave generating source. Nevertheless, this system receives a great deal of attention as it does not cause X-ray exposure and it can perform continuous monitoring.

In particular, since the ultrasonic imaging unit is a semi-real-time image diagnosing unit, it can continuously monitor the state of a calculus. Since continuous monitoring is possible, even if the position of the calculus is deviated from the focal point of a shock wave due to a respiratory movement or body movement of the patient, positional deviation can be immediately confirmed, and radiation of the shock wave is stopped in such a case.

When the ultrasonic imaging unit is in the medical application described above, it is especially significant to detect a small calculus of about 5 mm. For this purpose, in order to improve the resolution, a so-called multi-stage focus is used, or the number of scanning lines per frame is increased. In this case, a high-resolution image can be obtained over a wide range by decreasing the frame rate (repetition frequency of the ultrasonic image=frame count per second) of the ultrasonic imaging unit. The real-time characteristics of the ultrasonic imaging unit are sacrificed more or less.

Use of an apparatus for destroying a calculus having such an ultrasonic imaging unit in an actual clinical case will be described. A high-resolution image is required before detection of a calculus is started in order to obtain the position of the calculus on a screen displaying an ultrasonic image. Once treatment is started, the frame rate can be increased. This policy is applicable without any problem when a slow movement of a calculus such as a respiratory movement is to be monitored. However, if the high resolution of an image is achieved simply by decreasing the frame rate, the following problems arise. These problems will be described below.

The present inventors conducted the following experiment. In this experiment, a shock wave was radiated on a calculus placed in water to destroy the calculus. According to this experiment, when destruction of the calculus proceeded by shock wave radiation and small calculus fragments were started to be formed, the fragments were observed to jump in synchronism with shock wave radiation. This phenomenon is called a stone dance. A similar phenomenon was observed in destruction of a calculus in a human body. Accordingly, this stone dance can serve as effective information indicating the calculus destruction state. Since the stone dance, however, is a quick phenomenon, it was difficult to observe it on an ultrasonic image at a low frame rate.

In the apparatus for destroying a calculus of this type, a single radiation shock wave operation is insufficient in most cases and repetitive radiation over a multiple of times is usually performed. A radiation count until calculus destruction is completed varies depending on the type of the calculus, the figure of the patient, the depth of the location of the calculus from the body surface, the energy of the shock wave, and the like. Hence, to record and reserve a numerous treatment data is effective in appropriately setting the shock wave radiation count. It is indispensable in terms of improvement of the treatment efficiency and safety to grasp the treatment state as a treatment trend during treatment.

Regarding the treatment method, an erroneous radiation preventive treatment mode for radiating a shock wave once or continuously without damaging tissues around the calculus has started to be employed. An erroneous radiation preventive treatment mode is described in Published Unexamined Japanese Patent Application Nos. 60-191250, 61-149562, and so on.

The erroneous radiation preventive treatment mode is as follows. That is, when a piezo-electric device is used as a shock wave source, a fact that a wave reflected by the focal region of the shock wave can be received by the piezo-electric device is utilized. A weak ultra-sonic wave is transmitted and received by the piezo-electric device immediately before an intense shock wave is emitted. When an intense echo is received, it is determined that the focal region of the shock wave coincides with the calculus. When this determination is made, a shock wave is irradiated on the calculus.

This erroneous radiation preventive treatment mode cannot be applied to all patients, as an intense wave is not always reflected by the patient. If an intense wave is not reflected by the patient, first, shock waves are continuously radiated in accordance with the treatment mode. Along with the procedure of destruction, when an intense wave is started to be reflected by the patient, the erroneous radiation preventive treatment mode may be set in place of the treatment mode.

In an apparatus for destroying a calculus having a shock wave source using underwater discharge or a small explosion, a mode having a similar function to the erroneous radiation preventive treatment mode is provided in addition to the treatment mode for radiating the shock wave once or continuously. According to this mode, a shock wave is radiated only during the inspiration end period of the respiration so as not to damage the tissues around the calculus, or a shock wave is radiated in synchronism with the electrocardiogram. When this mode is set, a destruction treatment mode is sometimes changed to another destruction treatment mode during a single destruction treatment.

Regarding the destruction rate, the higher the destruction rate, the faster the treatment is completed naturally. When the destruction rate is increased, however, the patient feels pain, or the destruction pressure is decreased due to cavitation. Therefore, the rate must be changed to an optimum value on the basis of the judgement of the doctor.

In this manner, not only the destruction energy quantity (more particularly, the drive voltage of the shock wave source, e.g., the piezo-electric device, and the pressure of the shock wave) but also the destruction treatment mode and the destruction rate serve as significant factors in terms of the treatment efficiency and safety. However, the treatment trend of the conventional apparatus for destroying a calculus includes only the transition graph (the radiation count is plotted along the axis of abscissa) of the destruction energy and the patient data (e.g., name, age, patient's ID No., and name of the disease) which are insufficient to evaluate the treatment efficiency and grasp the safety.

According to the erroneous radiation preventive treatment mode described above, only an ultrasonic image or an X-ray image can be used to determine the destruction degree of a calculus, and such a determination is not so reliable. Thus, even if the apparatus has a function of radiating the shock wave only to the calculus, the shock wave can be radiated continuously even after destruction is completed. In this case, damage to the normal tissues around the calculus cannot be neglected, and the treatment time becomes longer than necessary. Inversely, if the dose of the shock wave is excessively small, another treatment section will be needed, and impaction of a large calculus fragment in an ureter may occur.

SUMMARY OF THE INVENTION

It is an object of the present invention to provide an apparatus for destroying a calculus which can position a shock wave source easily and which can monitor a destruction state properly.

It is another object of the present invention to provide an apparatus for destroying a calculus which can evaluate a treatment efficiency properly and which can display a treatment trend for confirming the safety.

It is still another object of the present invention to provide an apparatus for destroying a calculus which can properly radiate a shock wave only on a non-destroyed calculus, which minimizes a side-effect, and which has a high treatment efficiency.

The above objects are achieved by an apparatus for destroying a calculus, comprising:

shock wave radiating means for radiating a shock wave to a calculus in a living body;

first control means for controlling radiation of the shock wave;

acquiring means for acquiring morphological data of the living body; and second control means, cooperated with the shock wave radiating means, for controlling the acquiring means, so that the morphological data having a low time resolution is acquired when the shock wave is not radiated by control of the first control means and the morphological data having a high time resolution is acquired when the shock wave is radiated by control of the first control means.

The above objects are also achieved by an apparatus for destroying a calculus, comprising:

shock wave radiating means for radiating a shock wave to a calculus in a living body;

first control means, in which a predetermined treatment mode is set, for controlling repetitive radiation of the shock wave on the basis of the predetermined treatment mode;

data acquiring means for acquiring data concerning a destruction energy quantity based on the shock wave, data concerning a radiation rate of the shock wave, and data concerning a destruction treatment mode from the shock wave radiating means and the control means every time a predetermined radiation count of the shock wave is obtained;

calculating means for calculating first data indicating a change over time in destruction energy quantity with respect to the radiation count of the shock wave on the basis of the respective data acquired by the data acquiring means and second data indicating a change over time of at least one of the radiation rate and the destruction treatment mode on the basis of the respective data acquired by the data acquiring means; and display means for displaying the first and second data calculated by the calculating means on the same screen.

The above objects are also achieved by an apparatus for destroying a calculus, comprising:

ultrasonic wave generating means, including a plurality of ultrasonic wave generating elements, for generating an intense ultrasonic wave that serves as a shock wave when a high voltage is applied and a weak ultrasonic wave that does not serve as a shock wave when a low voltage is applied and for selectively radiating the intense and weak ultrasonic waves to a calculus in a living body;

drive means, including a plurality of drive elements, for driving the ultrasonic wave generating means by selectively supplying at least a low voltage and a high voltage to the ultrasonic wave generating elements of the ultrasonic wave generating means;

receiving means, including a plurality of receiving elements, for receiving an echo signal from the living body when the ultrasonic wave generating means is driven by the low voltage;

control means for controlling the drive means and the receiving means;

peak value detecting means for detecting a peak value, in a predetermined time width, of the echo signal in a reception signal received by the receiving means;

first comparing means for comparing the peak value detected by the peak value detecting means with a first predetermined threshold value;

frequency analyzing means for analyzing a frequency component, in the predetermined time width, of the echo signal in the reception signal;

calculating means for calculating a predetermined characteristic value on the basis of frequency component data obtained by the frequency analyzing means;

second comparing means for comparing the characteristic value obtained by the calculating means with a second predetermined threshold value; and display means for displaying a comparison result of the first comparing means and a comparison result of the second comparing means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 shows an arrangement of an apparatus for destroying a calculus according to the second embodiment of the present invention;

FIG. 6 shows another display example of treatment data of the second embodiment;

FIG. 12A shows an output voltage waveform when the drive circuit of FIG. 11 does not have a damping inductor, and FIG. 12B shows an output voltage waveform when the drive circuit of FIG. 11 has a damping inductor;

FIGS. 13A and 13B show spectral distributions of the output voltage waveforms of the drive circuits of FIGS. 10 and 11;

FIG. 15 shows an arrangement of an apparatus for destroying a calculus according to the fifth embodiment of the present invention.

DETAILED DESCRIPTION OF THE PREFERRED EMBODIMENTS

Figure 1:
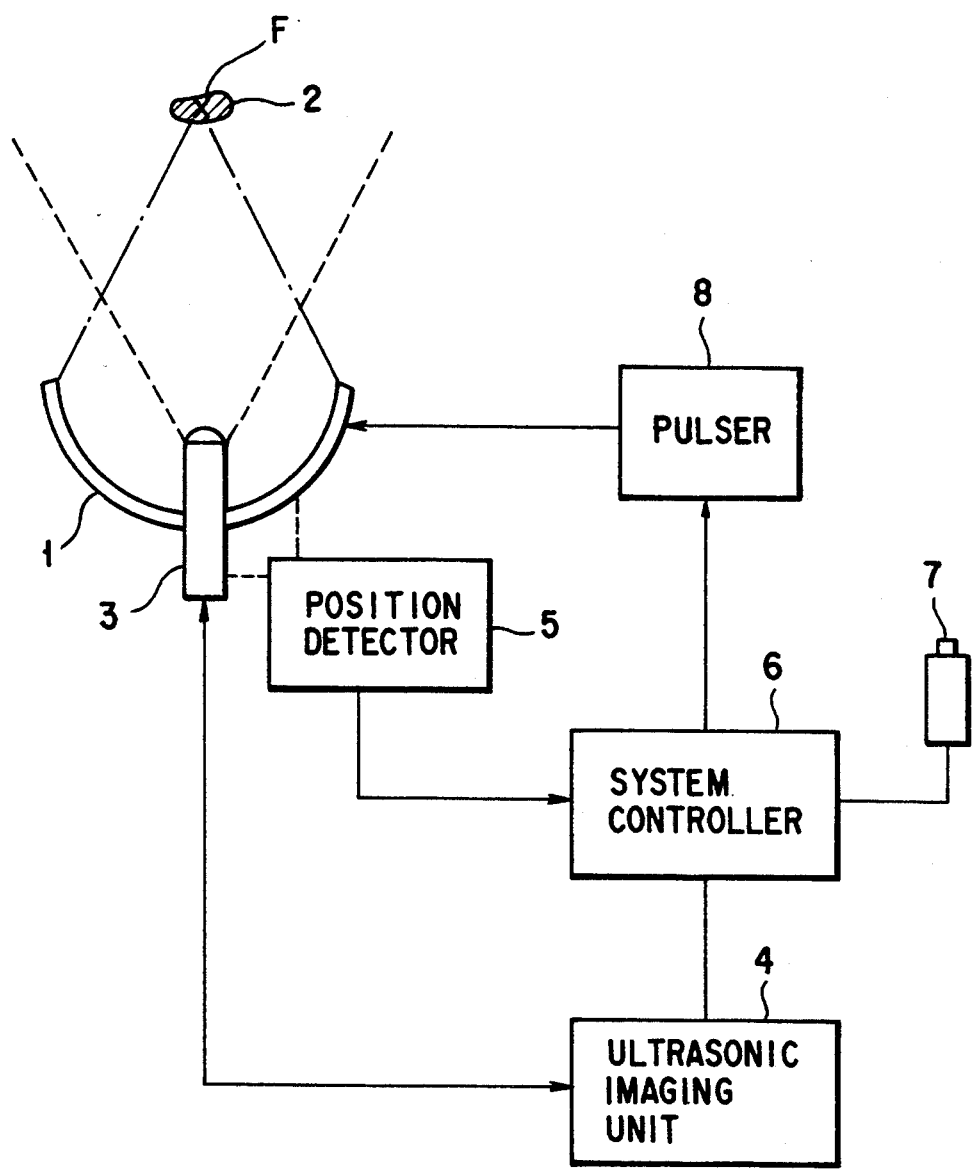
FIG. 1 is a schematic diagram showing an arrangement of an apparatus for destroying a calculus according to the first embodiment of the present invention.

The preferred embodiments of the present invention will be described with reference to the accompanying drawings. FIG. 1 shows an arrangement of an apparatus for destroying a calculus according to the first embodiment of the present invention.

A shock wave source 1 has, as major components, a spherical member (not shown) and a plurality of piezoelectric devices arranged on the inner surface of the spherical member to constitute a spherical shell.

The shock wave source 1 is supported by a known support unit (not shown) and can be manually moved. The shock wave source 1 can also be moved by a known mechanism (not shown) using an electric power, an electromagnetic force, or a fluid pressure. The shock wave source 1 is moved mainly to cause the focal point of the shock wave to coincide with the calculus.

The shock wave source 1 is driven by a high-voltage pulse supplied from a pulser 8 to generate a shock wave. The shock wave is focused on a focal point F as the geometric center of the spherical shell. A region near the focal point F is referred to as a focal region. An ultrasonic imaging probe 3 for drawing and positioning a calculus 2 is provided inside the shock wave source 1. The probe 3 is arranged at the center of the interior of the shock wave source 1. The probe 3 can slide back and forth and can rotate and is arranged in an ultrasonic imaging unit 4.

A typical example of the ultrasonic imaging unit 4 is an ultrasonic imaging unit SSA-270A manufactured by TOSHIBA CORPORATION. When an ultrasonic wave is transmitted to and received from a living body (not shown) by the probe 3, an ultrasonic image on a slice including the focal point F is drawn. In this embodiment, an electronic sector scanning probe is used as the probe 3. The ultrasonic imaging unit 4 can increase or decrease the number of focal points of the electronic focus during ultrasonic transmission or reception or both. More particularly, the ultrasonic imaging unit 4 can employ 4-stage focus in ultrasonic transmission. When 4-stage focus is performed, a high-resolution ultrasonic tomographic image can be obtained over the entire area of the screen.

A position detector 5 measures the relative positions (distance) of the shock wave source 1 and the probe 3. For example, a potentiometer is used as the position detector 5. The potentiometer is arranged in the shock wave source 1 so as to be cooperated with the forward and backward movements of the probe 3. The position detector 5 outputs position data of the probe 3 in the form of an electrical signal. The output signal from the position detector 5 is supplied to the ultrasonic imaging unit 4 through a system controller 6. The ultrasonic imaging unit 4 superimposes a marker indicating the position of the focal point F on the basis of the signal from the position detector 5.

Figure 2:
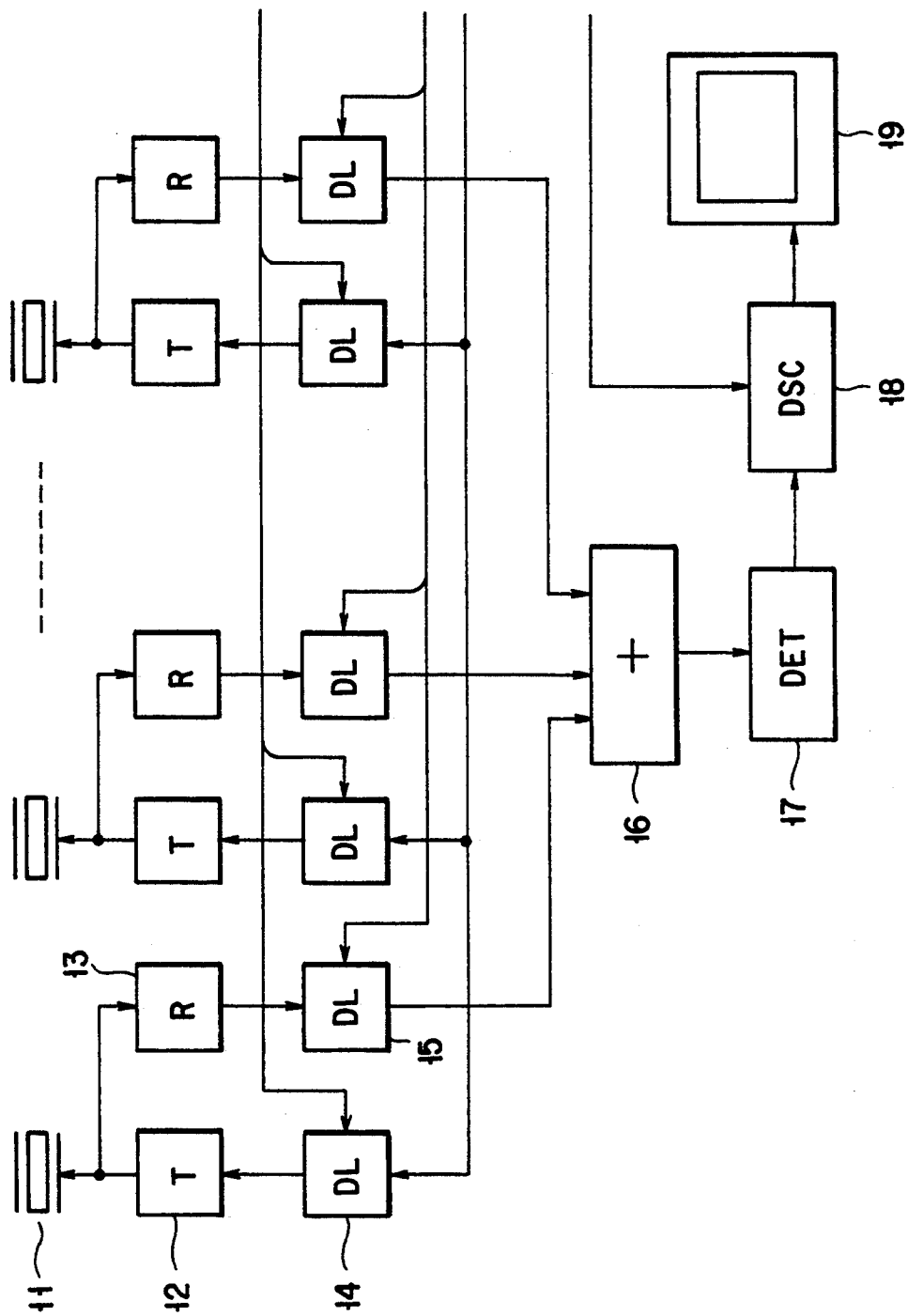
FIG. 2 shows an arrangement of an ultrasonic imaging probe and an ultrasonic imaging unit in detail.

FIG. 2 shows an arrangement of the ultrasonic imaging probe 3 and the ultrasonic imaging unit 4. The probe 3 has a plurality of ultrasonic transducers arranged therein. The ultrasonic wave can be deflected and electronically focused by phase-controlling each transducer 11 during ultrasonic transmission or reception or both. Each transducer 11 is connected to a transmission circuit 12 and a reception circuit 13. Each transmission circuit 12 receives a trigger pulse from the system controller 6 through a transmission delay circuit 14 to pulse-drive the corresponding transducer 11. The ultrasonic pulse emitted from the transducer 11 is radiated on the interior of the patient's body and reflected by a reflecting member, e.g., a calculus. The respective echoes are received by the transducers 11, amplified by the reception circuits 13, and supplied to an adder circuit 16 through reception delay circuits 15 to be added with each other. An output signal from the adder circuit 16 is detected by a detection circuit 17 and input to a DSC (Digital Scan Converter) 18 comprising an A/D converter, a digital image memory, a D/A converter, and the like. Image data obtained by the DSC 18 is supplied to a CRT display 19, and a B-mode tomographic image of the patient's body is displayed on the display 19 as an ultrasonic image.

The delay times of the transmission and reception delay circuits 14 and 15 are controlled by the system controller 6. That is, the respective ultrasonic transducers 11 are controlled by the corresponding transmission circuits 12 with relative delay time differences. During reception, the echo signals output from the reception circuits 13 are supplied to the adder circuit 16 with the same delay time differences as those in transmission, thereby focusing the ultrasonic beam. This focusing function of the ultrasonic beam by way of control of the delay time is called electronic focus. Control of the delay time described above realizes phase control.

In this case, a change in focal point of the electronic focus and formation of a plurality of focal points in one frame image are realized by controlling the delay time of at least either the transmission delay circuits 14 or the reception delay circuits 15 and by controlling an increase or decrease in number of transducers used for driving. This operation is known well as multi-stage focus or dynamic focus.

In this embodiment, the frame rate is decreased when the shock wave is radiated and increased when the shock wave is not radiated by the system controller 6 by changing the number of stages of the multi-stage focus, i.e., by changing the number of focal points. It suffices if multi-stage focus is employed only during transmission.

Figure 3A:
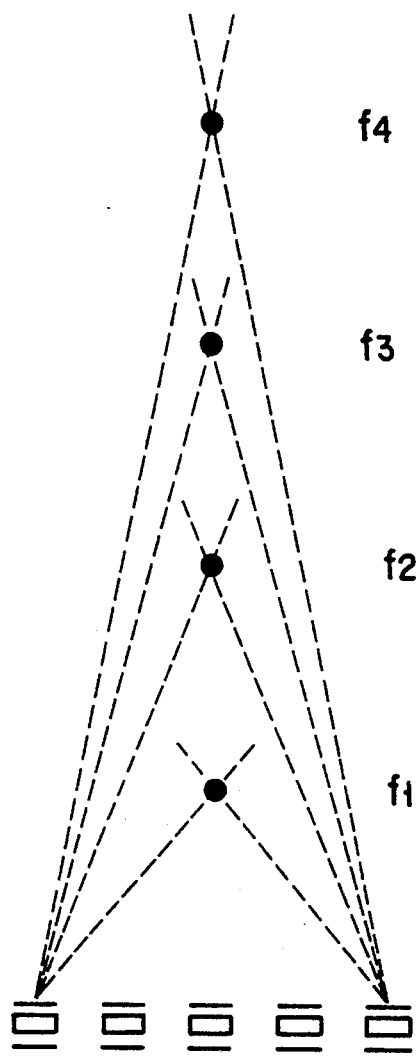
FIGS. 3A and 3B are views for explaining frame rate control by selection of the number of steps of a multistage focus of the first embodiment.
Figure 3B:
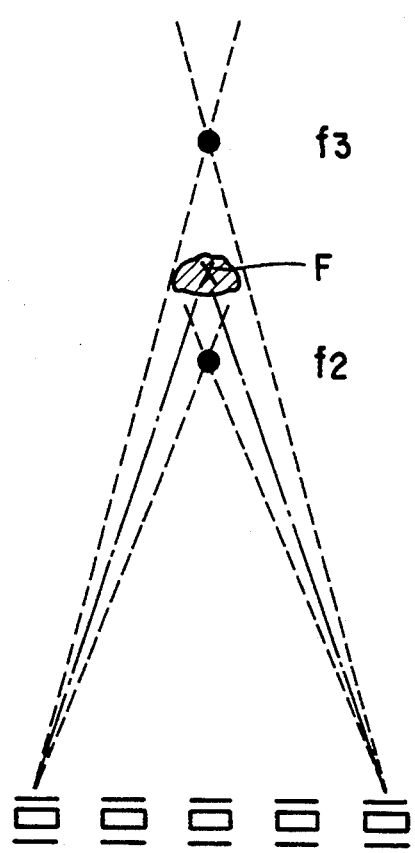

FIGS. 3A and 3B schematically show frame rate control. In this example, the number of stages of multi-stage focus is 4 at maximum, as shown in FIG. 3A, and four focal points f1 to f4 are formed. FIG. 3B shows a state in which the number of focal points is decreased to 2, i.e., the focal points f2 and f3.

In actual treatment, the operator moves the shock wave source 1 to cause the focal point F to coincide with the calculus 2 while he observes the ultrasonic screen. Movement of the shock wave source 1 is realized manually or non-manually, as described above. When the shock wave source 1 is to be moved non-manually, electricity, electromagnetic energy, or a fluid pressure is employed. During positioning, the system controller 6 controls the ultrasonic imaging unit 4 to be set in the multi-stage focus mode, i.e., such that the four focal points f1 to f4 are formed, as shown in FIG. 3A.

When positioning is completed, the operator depresses a treatment start/end switch 7 provided to the system controller 6 to instruct radiation start of the shock wave. The system controller 6 supplies a trigger to the pulser 8 in response to this instruction, and the pulser 8 drives the piezo-electric device group of the shock wave source 1 with a high voltage. At this time, the system controller 6 supplies treatment start data to the ultrasonic imaging unit 4 simultaneously. Then, the system controller 6 controls the ultrasonic imaging unit 4 until treatment is stopped such that its focal points are formed only in the vicinity of the focal point F of the shock wave source 1, e.g., only at two portions before and after the focal point F as the focal points f2 and f3, as shown in FIG. 3B.

As a result, the frame rate of the ultrasonic imaging unit 4 becomes twice that during multi-stage focus. When the probe 3 is moved back and forth during treatment, it is apparent that the positions of the focal points of the ultrasonic imaging unit 4 must be changed in accordance with the depth of the moved focal point F.

When the treatment is completed with the calculus being destroyed, or when the calculus is moved and repositioning is needed, the treatment start/end switch 7 is depressed again to stop the treatment. At this time, treatment stop data is supplied from the system controller 6 to the ultrasonic imaging unit 4 and the pulser 8, in a reverse order to the operation described above, to stop driving of the shock wave source i, and the initial multi-stage focus, i.e., the state shown in FIG. 3A is restored.

In this embodiment, the number of stages of variable focus is decreased in order to increase the frame rate. However, since scanning of the ultrasonic imaging unit 4 used for positioning of an apparatus for destroying a calculus of this type is generally of an electronic sector type, the same effect can be obtained even if the sector scanning angle of the ultrasonic image is decreased. The technique to change the sector scanning angle in a sector scanning-type ultrasonic imaging unit is known to a person skilled in the art. Accordingly, even if the condition of multi-stage focus is unchanged after the treatment is started, if the sector angle is decreased to half, the frame rate can be increased twice. Note that when the sector scanning angle is to be decreased during shock wave radiation, the sector scanning angle must be set such that the scanning range covers at least the focal region of the shock wave.

In this embodiment, a shock wave source using piezoelectric devices is employed. However, the present invention can similarly be applied to an underwater discharge or electromagnetic induction type shock wave source.

In this embodiment, an electronic sector scanning-type ultrasonic imaging unit is employed. However, an ultrasonic imaging unit, e.g., a mechanical sector type ultrasonic imaging unit using annular array vibrators whose frame rate is decreased when the resolution is increased in multi-stage focus can be used.

In this embodiment, the ultrasonic imaging probe 3 is arranged inside the shock wave source 1. However, it can be arranged outside the shock wave source 1.

The second embodiment of the present invention will be described with reference to FIG. 4. In the second embodiment, piezo-electric devices 21 as the shock wave source are mounted on a patient 23 through a coupling container 22 containing water as a medium to propagate an ultrasonic wave. The piezo-electric devices 21 are connected to a drive circuit 24. A high-voltage pulse is applied to each piezo-electric device 21 by the drive circuit 24 to generate shock wave. The shock wave is radiated on a calculus 25 positioned at the focal point of the piezo-electric devices 21 to perform destruction treatment of the calculus 25.

The apparatus for destroying a calculus according to the second embodiment further has a patient data input unit 26, a destruction voltage setter 27, a destruction rate setter 28, a destruction treatment mode setter 29, a system controller 30, a drive power supply 31, a transmitter 32, a memory controller 33, a destruction instruction switch 34, a storage unit 36, a display instruction switch 37, a display controller 38, and a CRT display 39.

The operation of the second embodiment will be described. Before start of a destruction treatment, patient data, e.g., the patient's name, the patient's ID No. (patient's identification code), and the comments of the doctors, are input to the system controller 30 by the patient data input unit 26. A destruction voltage, a destruction rate (e.g., 1 Hz), and a treatment mode (e.g., a continuous radiation mode) are set by the destruction voltage setter 27, the destruction rate setter 28, and the treatment mode setter 29, respectively, and data including the destruction voltage, the destruction rate, and the treatment mode are input to the system controller 30. The system controller 30 sets the destruction voltage data and the destruction rate data in the drive power supply 31 and the transmitter 32, respectively, and sets patient data, the destruction voltage data, the destruction rate data, and the treatment mode data in the main controller 33.

When the operator depresses the destruction instruction switch 34 to start destruction treatment, the system controller 30 outputs a destruction start pulse 35 to the transmitter 32 to instruct the start of destruction. In accordance with this instruction, the transmitter 30 outputs a radiation pulse at the preset destruction rate to activate the drive circuit 24. The drive circuit 24 drives the piezo-electric devices 21 with the preset destruction voltage. Thus, a shock wave is radiated from the piezo-electric devices 21 to the calculus 25.

In synchronism with this shock wave radiation, the main controller 33 is activated by the radiation pulse 30. The main controller 33 comprises a multiplexer and a counter and supplies data including the destruction voltage, the destruction rate, and the destruction treatment mode to the storage unit 36 sequentially every time it is activated by a radiation pulse. Thus, these data are stored in the storage unit 36 as treatment data.

Figure 5:
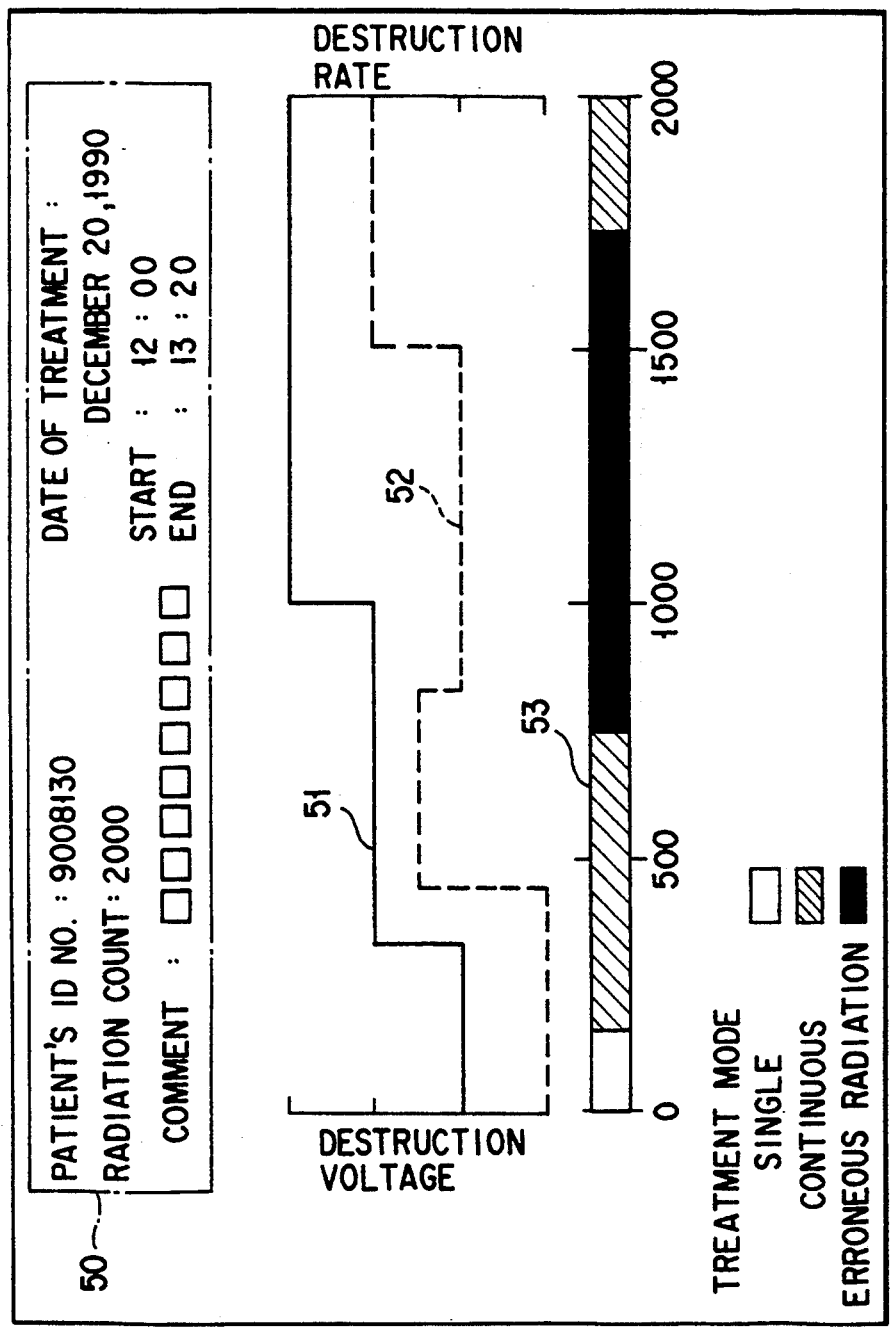
FIG. 5 shows a display example of treatment data of the second embodiment.

Subsequently, when the operator depresses the display instruction switch 37, the system controller 30 activates the display controller 38 comprising a graphic display controller and a character display controller to display the treatment data as shown in FIG. 5 on the CRT display 39 on the basis of the data in the storage unit 36.

The series of operations described above are continued until the destruction instruction switch 34 is turned off by the operator. When conditions set by the destruction voltage setter 27, the destruction rate setter 28, and the destruction treatment mode setter 29 are changed, the updated contents are stored as treatment data. The treatment data displayed on the CRT display 39 is sequentially updated during treatment. Accordingly, the operator can continue the treatment while he accurately grasps the situation by observing the displayed treatment data.

In the display example of the treatment data shown in FIG. 5, patient data 50 (in this example, the patient's ID No., the date of treatment, and the comment) is input to the patient data input unit 26 by a key operation. The axis of abscissa represents the radiation count of the shock wave (destruction energy wave). The axis of ordinate on the left side represents the destruction voltage and corresponds to a graph 51, and the axis of ordinate on the right side represents the destruction rate and corresponds to a graph 52. A pattern display 53 on the lower side represents the destruction treatment mode. In this manner, changes over time in destruction voltage, destruction rate, and treatment mode with respect to the shock wave radiation count can be displayed on one screen, and the operator can easily confirm the process of treatment from this display.

FIG. 6 shows another display example of treatment data. FIG. 6 is similar to FIG. 5 except that display of the destruction treatment mode is changed from the pattern display 53 of FIG. 5 to a character display 54.

In this embodiment, a display is given in black-and-white representation considering a print output. However, a display can be given in color representation by discriminating the respective data by different colors. In FIG. 6, the character display is used for displaying the destruction treatment mode. However, the character display can be used for displaying the destruction rate, and the axis of ordinate can represent the destruction treatment mode.

Regarding the shock wave source, other than the piezo-electric devices, underwater discharge, micro explosion, or electromagnetic induction type sources can be used.

The third embodiment of the present invention will be described with reference to FIG. 7.

Figure 7:
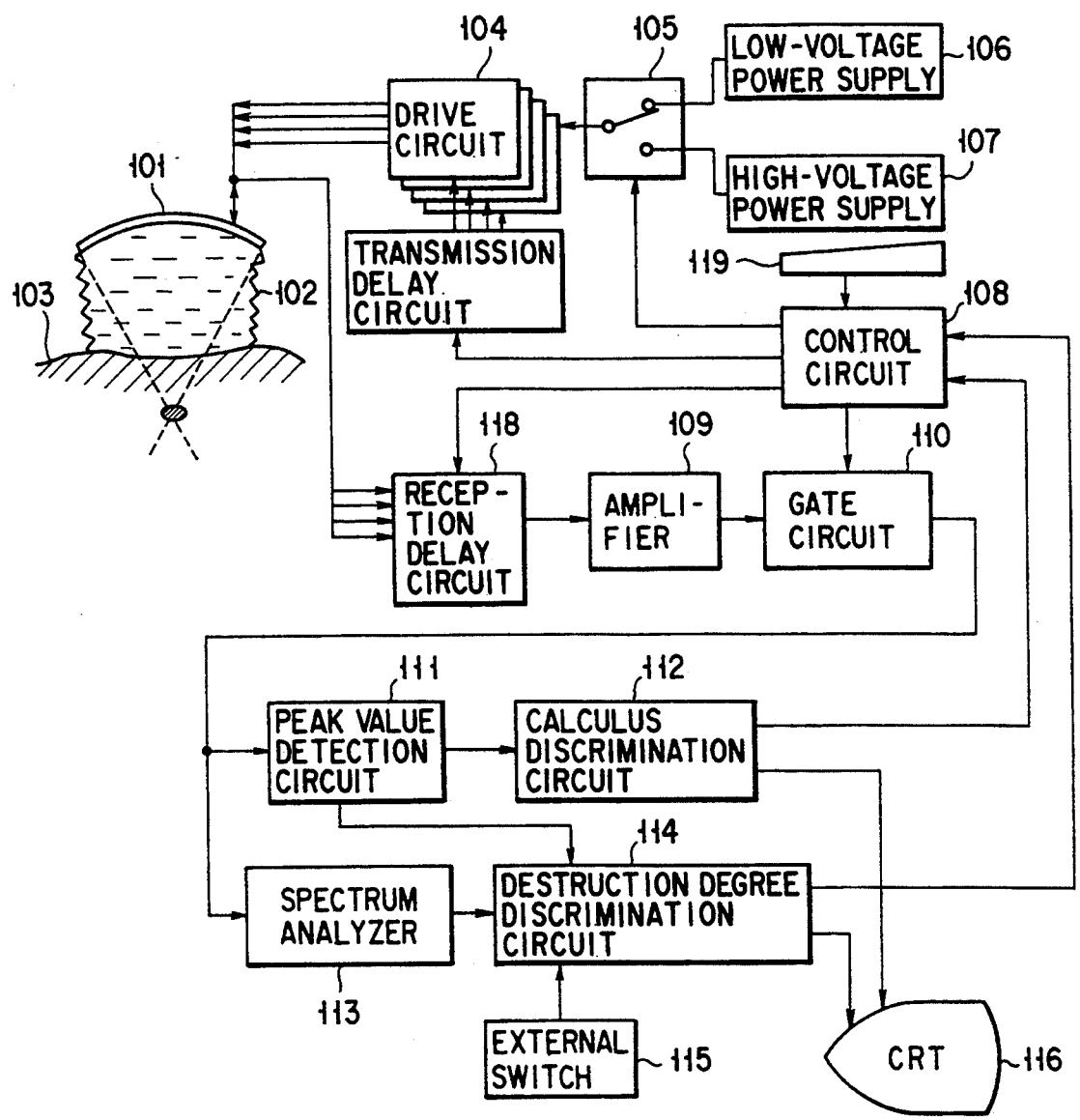
FIG. 7 shows an arrangement of an apparatus for destroying a calculus according to the third embodiment of the present invention.

Referring to FIG. 7, in a piezo-electric device group 101 as the shock wave source, all of the annular piezo-electric devices are concentrically arranged in a spherical shell-like shape such that the ultrasonic wave transmitting/receiving surface constitutes a recessed surface. The piezo-electric device group 101 is coupled to a patient 103 through a flexible water bag 102.

The piezo-electric device group 101 is connected to drive circuits 104 which are equal in number to the piezo-electric devices. The drive circuits 104 are selectively connected to either a low- or high-voltage power supply 106 or 107 through a selector switch 105 which is controlled by a control circuit 108.

The drive circuits 104 are also connected to a transmission delay circuit 117. The transmission delay circuit 117 comprises, e.g., a shift register which can delay a logic-level pulse. The delay amounts of the transmission delay circuit 117 are controlled by the control circuit 108 to supply trigger pulses to the drive circuits 104 at predetermined timings, thus controlling the application timings of the drive voltages to the respective piezo-electric devices. The delay amounts of the transmission delay circuit 117 are set such that the piezo-electric device group 101 has focal points substantially at positions instructed by an external switch (e.g., a keyboard) 119 when the shock wave is generated. Movement of the focal points by delay time control is known as it is described in detail in, e.g., U.S. Pat. No. 4,526,168, and thus a detailed description thereof is omitted.

An RF signal (echo signal) obtained by the piezoelectric device group 101 by receiving an echo from the interior of the body of the patient 103 is input to an amplifier 109 through a reception delay circuit 118. The reception delay circuit 118 comprises an analog delay circuit and its delay amounts are controlled by the control circuit 108 in the same manner as the transmission delay circuit 117. Thus, the piezo-electric device group 101 has focal points in reception at substantially the same positions as in the shock wave generation.

A gate circuit 110 is controlled by a gate signal from the control circuit 108 and extracts, of the echo signals output from the amplifiers 109, only those from the focal region of the piezo-electric device group 101. An output from the gate circuit 110 is input to a peak value detection circuit 111 and a spectrum analyzer 113.

The peak value detection circuit 111 detects a peak value (maximum amplitude) of the echo signal output from the gate circuit 110 and supplies it to a calculus discrimination circuit 112. The calculus discrimination circuit 112 compares the peak value detected by the peak value discrimination circuit 111 with a first preset threshold value TH1, and supplies the comparison result to the control circuit 108 and data representing the comparison state to a CRT display 116, respectively.

The spectrum analyzer 113 frequency-analyzes the echo signal output from the gate circuit 110 and supplies digital data representing a frequency component to a destruction degree discrimination circuit 114 as the analysis result. The destruction degree discrimination circuit 114 calculates a characteristic value concerning data of the input frequency component and compares it with a second preset threshold value TH2. The discrimination circuit 114 then supplies the comparison result to the control circuit 108 and to the CRT display 116. The practical arrangement of the destruction degree discrimination circuit 114 will be described later in detail.

The operation of the apparatus for destroying a calculus of this embodiment will be described.

In the initial state, the selector switch 105 is kept set on the low-voltage power supply 106 side. When the operator operates a treatment start switch (not shown), the drive circuits 104 are activated by trigger pulses from the treatment delay circuit 117. Then, the piezoelectric device group 101 is driven by a low-voltage pulse to emit a weak ultrasonic pulse which does not serve as a shock wave. This ultrasonic pulse is radiated on the interior of the body of the patient 103 through water in the water bag 102 as the propagating medium and focused in a focal region set by the delay times of the transmission delay circuit 117.

The ultrasonic pulse radiated on the interior of the body is reflected by portions having different acoustic impedances. These echoes are received by the piezoelectric device group 101. Of the echo signals received by the piezo-electric device group 101, those from the focal region set by the reception delay circuit 118, i.e., those from the focal region set by the transmission delay circuit 117 are supplied to the amplifier 109.

The echo signals are input to the gate circuit 110 to extract only those from the focal region of the piezoelectric device group 101. This can be achieved if the control circuit 108 supplies a gate signal to the gate circuit 110 to perform sampling when a reciprocal time required for an ultrasonic wave to reciprocate between the piezo-electric device group 101 and the focal points has elapsed after the drive circuits 104 generate low-voltage pulses. The echo signal from the focal region detected by the gate circuit 110 is supplied to the peak value detection circuit 111 to detect its peak value. The calculus discrimination circuit 112 mainly comprises a comparator to compare a peak value with the threshold value TH1.

An output signal from the gate circuit 110 is also input to the spectrum analyzer 113 to analyze its frequency component. The frequency component data output from the spectrum analyzer 113 is input to the destruction degree discrimination circuit 114. The destruction degree discrimination circuit 114 comprises, e.g., a digital signal processing circuit to normalize the input frequency component data by an output from the peak value detection circuit 111, obtains the intensity of a normalized data component having a specific frequency (e.g., 150 kHz), and calculates a ratio of this intensity to a preset value as a characteristic value concerning the frequency component. The preset value in this case can be stored in advance or can be intensity data having a 150-kHz component as an acquisition timing determined by an external switch 115 in order to input data of a calculus immediately before destruction. Then, the ratio obtained in this manner is compared with the threshold value TH2. The threshold value TH2 can be stored in advance or can be input through the external switch 115. The destruction degree of the calculus, i.e., whether destruction is completed or not, can be determined in this manner.

The effectiveness of this destruction degree discriminating method is also apparent from the results of an experiment conducted by the present inventors concerning the principle described above with reference to the function of the present invention. That is, the present inventors measured the frequency components of a spherical model calculus made of activated alumina and of different sizes of fragments of the same material. In order to decrease the influences of variation in echo intensity, the echo signal was normalized by a peak value and frequency-analyzed by a spectrum analyzer. It was observed that, starting from a spherical calculus, the smaller the destruction fragments, the smaller the peak value of about 150 to 200 kHz.

Accordingly, in the destruction degree circuit 114, the frequency component data supplied from spectrum analyzer 113 is normalized to obtain the ratio of the intensity of the 150-kHz component to the preset value and this ratio is compared with the threshold value TH2, in the manner as described above. If the ratio is larger than the threshold value TH2, it can be determined that a calculus which is not yet destroyed is present in the focal region; if the ratio is smaller than the threshold value TH2, it can be determined that the calculus is sufficiently destroyed.

The comparison results of the calculus discrimination circuit 112 and the destruction degree discrimination circuit 114 are supplied to the control circuit 108. In the initial state, the control circuit 108 keeps connecting the selector switch 105 to the low-voltage power supply 106 side, as described above. When a comparison result "the peak value is larger than the threshold value TH1" is input from the calculus discrimination circuit 112 and a comparison result "the ratio is larger than the threshold value TH2" is input from the destruction degree discrimination circuit 114, it is determined by the control circuit 108 that a calculus which is not yet destroyed is present in the focal region of the piezo-electric device group 101, and the selector switch 105 is switched to the high-voltage power supply 107 side. Accordingly, the piezo-electric device group 101 are driven by a high-voltage pulse by the drive circuits 104 to generate a shock wave. The radiation of the shock wave is focused in the focal region through the water bag 102 to destroy a calculus in the focal region.

This destruction operation is repeated until at least one of the two comparison results described above is reversed in the control circuit 108. That is, when a comparison result "the peak value is smaller than the threshold value TH1" is input from the calculus discrimination circuit 112 to the control circuit 108 or when a comparison result "the ratio is smaller than the threshold value TH2" is input from the destruction degree discrimination circuit 114 to the control circuit 108, it is determined by the control circuit 108 that destruction of the calculus is completed, and the selector switch 105 is switched to the low-voltage power supply 106 side.

Figure 8:
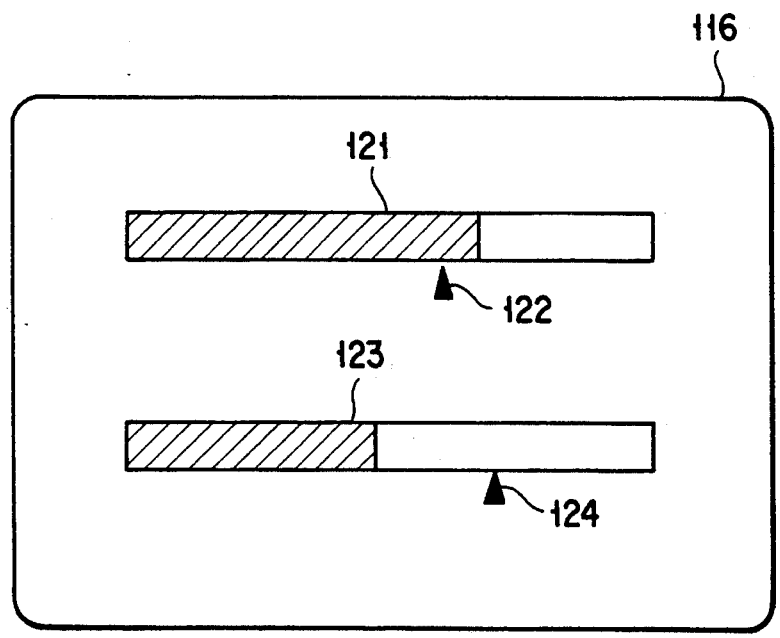
FIG. 8 shows a display example on a CRT display of FIG. 7.
Figure 9:
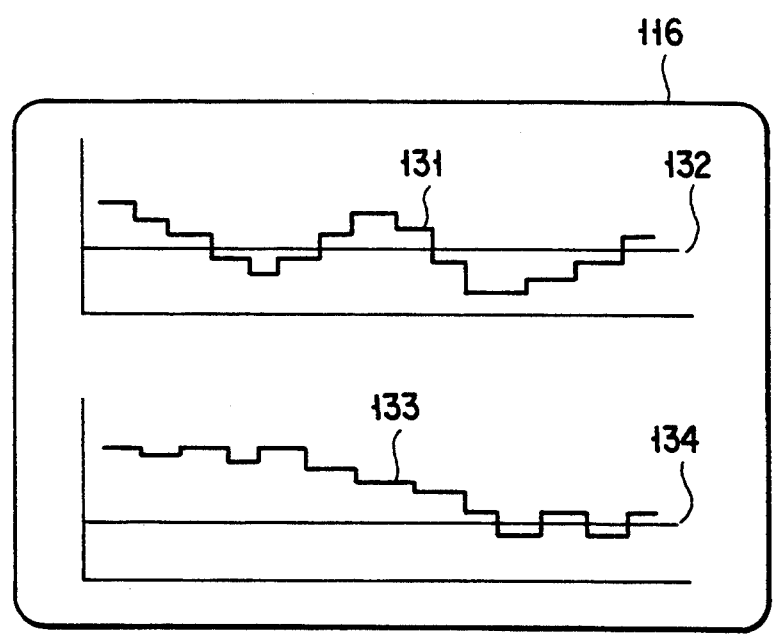
FIG. 9 shows another display example on the CRT display of FIG. 7.

The CRT display 116 displays a comparison result of the calculus discrimination circuit 112, i.e., the relationship between the peak value of the echo signal from the focal region and the threshold value TH1 and the comparison result of the destruction degree discrimination circuit 114, i.e., the relationship between the characteristic value concerning the frequency component of the echo signal from the focal region and the threshold value TH2. FIGS. 8 and 9 show display examples of the CRT display 116.

In FIG. 8, the peak value compared by the calculus discrimination circuit 112 and the ratio obtained by the destruction degree discrimination circuit 114 are displayed by way of the lengths of bars 121 and 123, respectively, and pointers 122 and 124 indicating the threshold values TH1 and TH2, respectively, are displayed in the vicinities of the bars 121 and 123, respectively. If the CRT display 116 is a color display, the threshold values TH1 and TH2 can be displayed by bar representation, in place of the pointers 122 and 124, by changing the color before and after the threshold values.

In FIG. 9, the peak value compared by the calculus discrimination circuit 112 and the ratio obtained by the destruction degree discrimination circuit 114 are displayed by graphs 131 and 133 of broken lines (or histograms), respectively, in which time is plotted along the axis of abscissa, and lines 132 and 134 indicating the threshold values TH1 and TH2, respectively, are displayed. Two types of graphs of broken lines can be displayed in the same display region, and the threshold values TH1 and TH2 can be displayed by a single common line. It is also possible to display a histogram, in place of a graph of broken line, by plotting time along the axis of abscissa.

The operator can move the piezo-electric device group 101 while observing this display to perform positioning such that its focal point coincides with a portion of a calculus which is not yet destroyed. Also, the operator can confirm the state of coincidence between the focal point of the piezo-electric device group 101 and the calculus or the destruction state of the calculus from this display and can operate the selector switch 105 manually.

Figure 10:
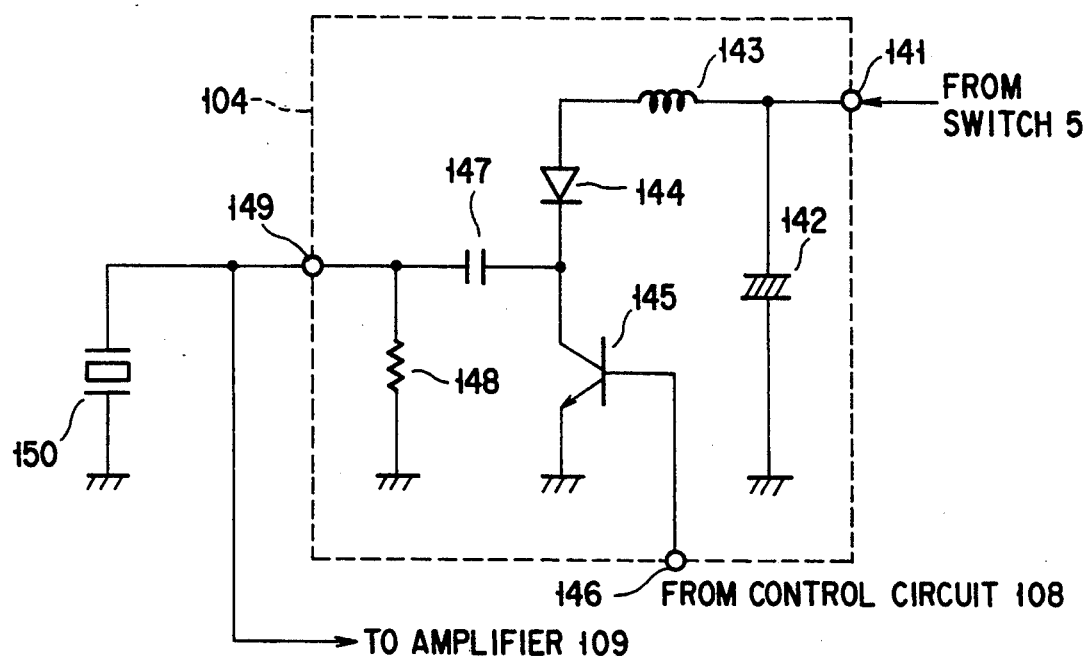
FIG. 10 is a circuit diagram showing an arrangement of a drive circuit of FIG. 7.

The drive circuits 104 of FIG. 7 will be described. FIG. 10 shows an arrangement of a drive circuit 104.

Referring to FIG. 10, a power supply input terminal 141 is connected to one terminal of a charge storage capacitor 142 and to an anode of a damping diode 144 through a resonance inductor 143. The cathode of the diode 144 is connected to the collector of a switching transistor 145 and one terminal of a coupling capacitor 147. The other terminal of the capacitor 147 is connected to a damping resistor 148 and an output terminal 149. The output terminal 149 is connected to a piezo-electric device 150 of the piezo-electric device group 101 of FIG. 7. The other terminal of the capacitor 142, the emitter of the transistor 145, and the other terminal of the resistor 148 are grounded. The base of the transistor 145 is connected to the control circuit 118 of FIG. 7 through a control input terminal 146.

When a control pulse is applied to the base of the transistor 145 through the control input terminal 146 to turn on the transistor 145, the charge stored in the capacitor 142 is discharged through the inductor 143, the diode 144, and the transistor 145 to gradually decrease the potential at the output terminal 149. Subsequently, when the transistor 145 is turned off, a counter electromotive force is generated in the inductor 143 to increase the potential at the output terminal 149 in the positive direction.

The inductance of the inductor 143 is selected to be tuned to the frequency of the mechanical resonance of the piezo-electric device 150, and the pulse width of the control pulse supplied to the control input terminal 146 is set to a reciprocal number of ½ the resonance frequency of the piezo-electric device 150. As a result, the output terminal 149 outputs a pulse voltage whose P-P (Peak-to-Peak) value is substantially twice the voltage of the low- or high-voltage power supply 116 or 117 as the drive voltage of the piezo-electric device 150.

Figure 11:
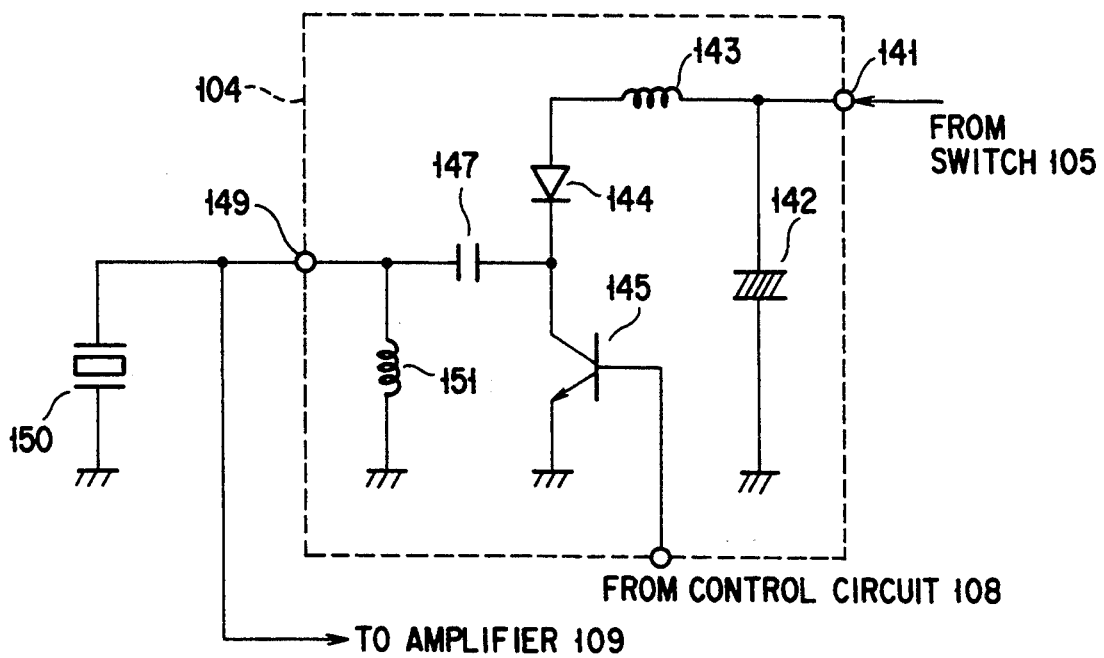
FIG. 11 is a circuit diagram showing another arrangement of the drive circuit of FIG. 7.

FIG. 11 shows another arrangement of a drive circuit 104. In this drive circuit, an inductor 151 is used as a damping element in place of the resistor 148 of FIG. 10. In this case, the inductance of the damping inductor 151 is set such that the resonance frequency determined by the inductance of the inductor 151 and the capacitance of the piezo-electric device 150 falls within a range of 100 to 250 kHz.

The operation of the damping inductor 151 of the drive circuit shown in FIG. 11 will be described. FIG. 12A shows a voltage waveform at the output terminal 149 when the circuit of FIG. 11 does not have the damping inductor 151, and FIG. 12B shows a voltage waveform at the output terminal 149 when the circuit of FIG. 11 has the damping inductor 151. When the drive circuit does not have the damping inductor 151, it takes time for the voltage at the output terminal 149, which is decreased by driving the piezo-electric device 150, to return to an original voltage level Vo, as shown in FIG. 12A. A low-frequency oscillation can be superposed on a high-frequency oscillation amplitude and thus a precise echo amplitude cannot sometimes be obtained.

When a damping inductor 151 is added, a low-frequency oscillation which occurs next to a drive voltage waveform when the piezo-electric device 150 is driven is quickly attenuated, as shown in FIG. 12B, and the voltage at the output terminal 149 is immediately returned to the original voltage level Vo. Therefore, the echo is not adversely affected. Thus, when the damping inductor 151 is added, accurate position data of the calculus can be easily obtained from the echo.

FIG. 13A shows a frequency spectrum of the drive voltage pulse when the resistor 148 is connected as a damping element in parallel to the piezo-electric device 150, as shown in FIG. 10, and FIG. 13B shows a frequency spectrum of the drive voltage pulse when the inductor 151 is connected in parallel to the piezo-electric device 150, as shown in FIG. 11. In the circuit of FIG. 10, the spectrum is distributed with respect to a resonance frequency fo of the piezo-electric device 150 as the center, as shown in FIG. 13A. In contrast to this, when the inductor 151 is added, as in FIG. 11, the spectrum has a peak in another frequency range fp which is determined by the inductance of the inductor 108 and the capacitance of the piezo-electric device 150, in addition to the peak at the resonance frequency fo of the piezo-electric device 150.

Accordingly, when the inductance of the inductor 151 is set such that the frequency range fp is given as a range of 150 to 200 kHz satisfying Ka<1 which concerns the discrimination of the destruction degree described above, the energy of this frequency range can be greatly imparted to the drive waveform itself.

As a result, the S/N ratio of the peak value signal which appears when the echo is analyzed by the spectrum analyzer 113 can be increased. The destruction state of the calculus from the characteristic value calculated in the above manner can be easily discriminated from the peak value. Monitoring of the destruction degree of the calculus by the echo can be performed more easily.

If a damping element is the resistor 148, as in the drive circuit of FIG. 10, the damping resistor 148 having a high breakdown voltage is needed so that its resistor wire will not be burned when it is driven with a high voltage. For this purpose, the resistor 148 must have a large size.

In contrast to this, if the inductor 151 is used as the damping element, as in the drive circuit of FIG. 11, since a resistor wire is not used, a high breakdown-voltage element whose wire will not be burned when driven with a high voltage can be easily realized. This damping element can have a considerably small size when compared to the resistor 148 as the damping element.

Figure 14:
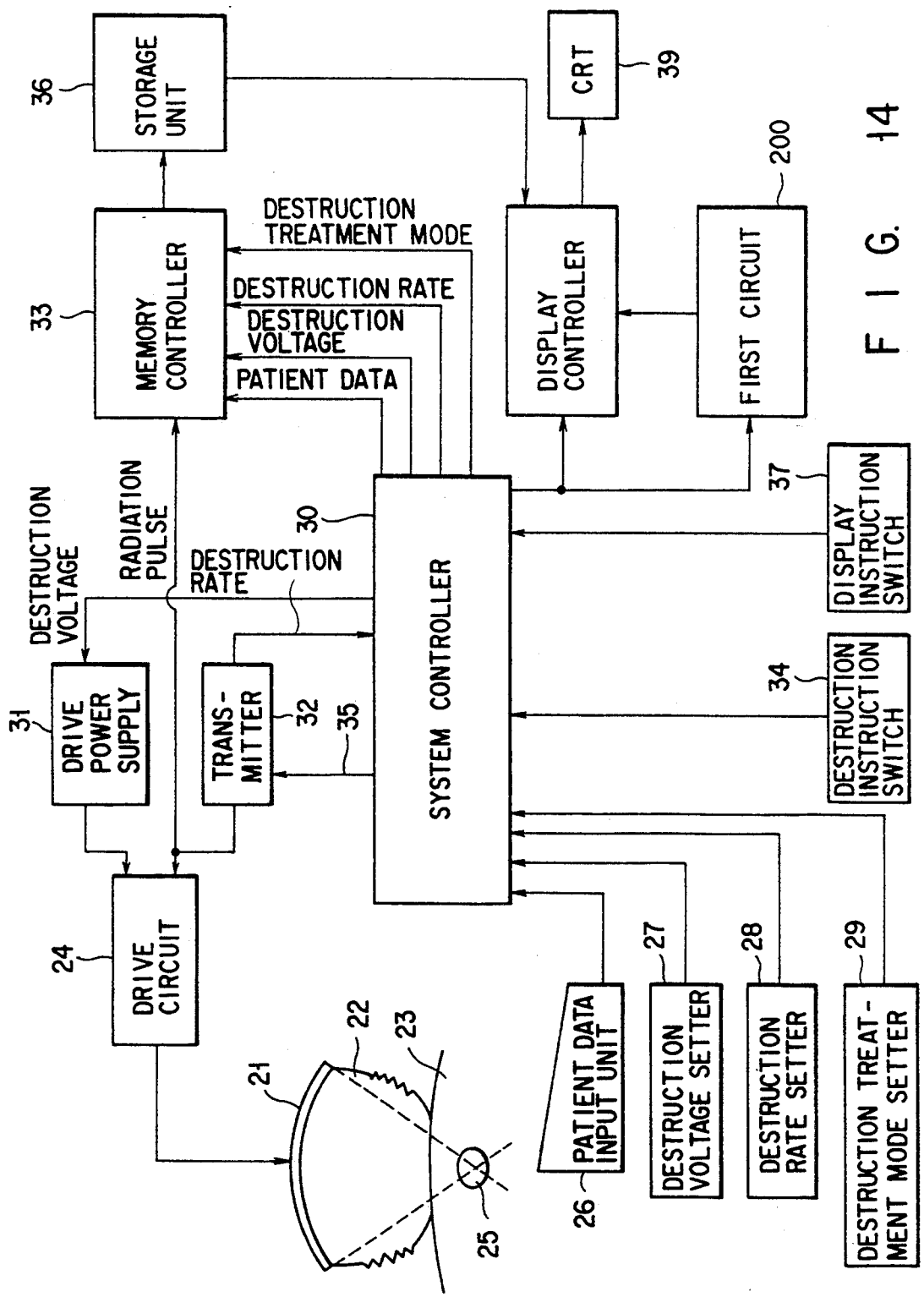
FIG. 14 shows an arrangement of an apparatus for destroying a calculus according to the fourth embodiment of the present invention.

The fourth embodiment of the present invention will be described with reference to FIG. 14. In the fourth embodiment, the main part of the third embodiment shown in FIG. 7 is applied to the second embodiment shown in FIG. 4. That is, a first circuit 200 shown in FIG. 14 includes the main part of the third embodiment shown in FIG. 4. Accordingly, the first circuit 200 includes the peak value detection circuit 111, the calculus discrimination circuit 112, the spectrum analyzer 113, the destruction degree discrimination circuit 114, the external switch 115, and the like of FIG. 7. According to the fourth embodiment having this arrangement, an apparatus for destroying a calculus having the functions of both the second and third embodiments can be provided.

The fifth embodiment of the present invention will be described with reference to FIG. 15. In the fifth embodiment, the main part of the second embodiment shown in FIG. 4 is applied to the third embodiment shown in FIG. 7. That is, a second circuit 300 shown in FIG. 15 includes the main part of the second embodiment shown in FIG. 4. Accordingly, the second circuit 300 includes the patient data input unit 26, the destruction voltage setter 27, the destruction rate setter 28, the destruction treatment mode setter 29, part of the system controller 30, the memory controller 33, the destruction instruction switch 34, the storage unit 36, the display instruction switch 37, the display controller 38, and the like of FIG. 4. According to the fifth embodiment having this arrangement, an apparatus for destroying a calculus having the functions of both the second and third embodiments can be provided.

The present invention can be modified in various manners as follows:

(a) In the above embodiments, the comparison results of the peak value of the echo signal and the characteristic value indicating the destruction degree with the respective threshold values are visually displayed by using the CRT display 116. However, the comparison results can be represented by sounds. More specifically, e.g., the peak value may be expressed by a sound volume, and the characteristic value may be expressed by a timbre. It is also possible to combine an audio representation with a visual representation of the CRT display 116.

(b) In the above embodiments, the drive voltages of the piezo-electric devices 101 are switched between two stages as low and high voltages. However, the drive voltage can be varied in a multi-stage manner or continuously and can be gradually changed as the destruction progresses.

(c) In the above embodiments, the discrimination of a calculus is performed by using a maximum amplitude of an echo. However, this discrimination can be performed by using an absolute value of an intensity of a certain single frequency (e.g., 150 kHz) before normalization, or an energy (an area of the spectrum) of a certain frequency range (e.g., 130 to 180 kHz) including this single frequency.

(d) According to the present invention, destruction treatment can be performed while discriminating whether an object which strongly reflects an ultrasonic wave is a calculus or not with the same arrangement as the above embodiments by utilizing the fact that the frequency component of an echo signal from a bone or air (a gas in the lung or intestine) in the body is different from that of an echo signal from a calculus.

(e) In the above embodiments, the ratio of the normalized intensity of the component of a single frequency (e.g., 150 kHz) of an echo signal from the focal region to a preset value is calculated as a characteristic value by the destruction degree discrimination circuit 114. However, a normalized energy (an area of the spectrum) of a certain frequency range (e.g., 130 to 180 kHz) including this frequency may be calculated, the change in normalized energy, i.e., the ratio of the normalized energy to a preset value, may be calculated as a characteristic value, and this ratio may be compared with the second threshold value. Then, the apparatus can withstand against noise compared to a method of obtaining the characteristic value from the component of a single frequency. In this, even if the spectrum analyzer 113 is not used, a band-pass filter and an amplitude detection circuit are combined to obtain substantially the same result as described above.

(f) In the above embodiments, normalization is performed by using the amplitude of a reception signal. However, even if the total energy or the energy of a predetermined frequency range is used, substantially the same result can be obtained.

(g) According to another arrangement of the destruction degree discrimination circuit 114, the frequency of the center of gravity of an energy in a certain frequency range (e.g., 100 to 200 kHz) including the specific frequency (e.g., 150 kHz) described above may be obtained, a ratio of the obtained frequency of the center of gravity to a preset value may be determined as the characteristic value, and the characteristic value may be compared with the second threshold value TH2. That is, as described above with reference to the function, as far as the size of the reflecting member is the same, the lower the frequency, the smaller the echo intensity. Accordingly, the smaller the size of the calculus, the higher the frequency of the center of gravity, and the larger the ratio of the frequency of the center of gravity to the preset value.

(h) In the above embodiments, a CRT is used as a means for conveying data to the operator. However, e.g., the intensity of the echo can be expressed by the intensity of a sound, and the degree of destruction can be expressed by a timbre. Also, audio representation and visual representation by the CRT can be combined.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for destroying a calculus, comprising:
   ultrasonic wave generating means, including a plurality of ultrasonic wave generating elements, for generating an intense ultrasonic wave that serves as a shock wave when a high voltage is applied and a weak ultrasonic wave that does not serve as a shock wave when a low voltage is applied and for selectively radiating the intense and weak ultrasonic waves to a calculus in a living body;
   drive means, including a plurality of drive elements, for driving said ultrasonic wave generating means by selectively supplying at least one low voltage and one high voltage to said ultrasonic wave generating elements of said ultrasonic wave generating means;
   receiving means, including a plurality of receiving elements, for receiving an echo signal from the living body when said ultrasonic wave generating means is driven by the low voltage and radiates the weak ultrasonic waves to the calculus in the living body;
   first control means for controlling said drive means and said receiving means;
   peak value detecting means for detecting a peak value, in a predetermined time width, of the echo signal in a reception signal received by said receiving means;
   first comparing means for comparing the peak value detected by said peak value detecting means with a first predetermined threshold value;
   frequency analyzing means for analyzing a frequency component, in the predetermined time width, of the echo signal in the reception signal;
   first calculating means for calculating a predetermined characteristic value on the basis of frequency component data obtained by said frequency analyzing means;
   second comparing means for comparing the characteristic value obtained by said calculating means with a second predetermined threshold value; and
   display means for displaying destruction degree information of the calculus defined by a comparison result of said first comparing means and a comparison result of said second comparing means, wherein said display means displays first data indicating a relationship between the peak value and the first predetermined threshold value and second data indicating a relationship between the characteristic value and the second predetermined threshold value.

2. An apparatus for destroying a calculus, comprising
   ultrasonic wave generating means, including a plurality of ultrasonic wave generating elements, for generating an intense ultrasonic wave that serves as a shock wave when a high voltage is applied and a weak ultrasonic wave that does not serve as a shock wave when a low voltage is applied and for selectively radiating the intense and weak ultrasonic waves to a calculus in a living body;
   drive means, including a plurality of drive elements, for driving said ultrasonic wave generating means by selectively supplying at least one low voltage and one high voltage to said ultrasonic wave generating elements of said ultrasonic wave generating means;
   receiving means, including a plurality of receiving elements, for receiving an echo signal from the living body when said ultrasonic wave generating means is driven by the low voltage and radiates the weak ultrasonic waves to the calculus in the living body;
   first control means for controlling said drive means and said receiving means;
   peak value detecting means for detecting a peak value, in a predetermined time width, of the echo signal in a reception signal received by said receiving means;
   first comparing means for comparing the peak value detected by said peak value detecting means with a first predetermined threshold value;
   frequency analyzing means for analyzing a frequency component, in the predetermined time width, of the echo signal in the reception signal;
   first calculating means for calculating a predetermined characteristic value on the basis of frequency component data obtained by said frequency analyzing means;
   second comparing means for comparing the characteristic value obtained by said calculating means with a second predetermined threshold value; and
   display means for displaying destruction degree information of the calculus defined by a comparison result of said first comparing means and a comparison result of said second comparing means, wherein said display means displays first data indicating a relationship between the peak value and the first predetermined threshold value and second data indicating a relationship between the characteristic value and the second predetermined threshold value by means of at least one of a visual representation and an audio representation.

* * * * *

UNITED STATES PATENT AND TRADEMARK OFFICE
CERTIFICATE OF CORRECTION

PATENT NO.  : 5,358,466
DATED       : October 25, 1994
INVENTOR(S) : Satoshi AIDA, et al.

It is certified that error appears in the above-indentified patent and that said Letters Patent is hereby corrected as shown below:

On the title page, Item [30], the first Foreign Application Priority Number is listed incorrectly. It should read:

--3-111044--

Signed and Sealed this

Fourth Day of April, 1995

Attest:

BRUCE LEHMAN

*Attesting Officer*   *Commissioner of Patents and Trademarks*